United States Patent [19]

Sinn

[11] Patent Number: 5,392,903
[45] Date of Patent: Feb. 28, 1995

[54] PACKAGE FOR RETAINING SURGICAL SUTURES

[75] Inventor: Hans-Jurgen F. Sinn, Fairfield, Conn.

[73] Assignee: United States Surgical Corporation, Norwalk, Conn.

[21] Appl. No.: 897,322

[22] Filed: Jun. 11, 1992

[51] Int. Cl.$^6$ ............................................. A61B 17/06
[52] U.S. Cl. ................................. 206/63.3; 206/394; 206/526
[58] Field of Search .................. 206/63.3, 227, 380, 206/394, 397, 495, 526

[56] References Cited

U.S. PATENT DOCUMENTS

| | | |
|---|---|---|
| D. 263,505 | 3/1982 | Black . |
| D. 265,972 | 8/1982 | Black . |
| 491,315 | 2/1893 | Lee .................... 206/63.3 |
| 2,142,707 | 1/1939 | Austin . |
| 2,643,765 | 6/1953 | Bradshaw ............ 206/63.3 |
| 3,095,159 | 6/1963 | Stacy et al. . |
| 3,112,825 | 12/1963 | Hammond et al. . |
| 3,127,992 | 4/1964 | Horine . |
| 3,185,299 | 5/1965 | Trainer . |
| 3,301,393 | 1/1967 | Regan, Jr. et al. ... 206/63.3 |
| 3,319,783 | 5/1967 | Henrici et al. ....... 206/526 |
| 3,326,369 | 6/1967 | Tolaas et al. ......... 206/526 |
| 3,376,973 | 4/1968 | Granowitz et al. . |
| 3,481,690 | 12/1969 | Edgworth . |
| 3,545,608 | 12/1970 | Berger . |
| 3,648,949 | 3/1972 | Berger et al. . |
| 3,731,793 | 5/1973 | Hagel ................... 206/63.3 |
| 3,749,238 | 7/1973 | Taylor . |
| 4,084,692 | 4/1978 | Bilweis . |
| 4,491,222 | 1/1985 | Gaccetta et al. ...... 206/394 |

FOREIGN PATENT DOCUMENTS

| | | |
|---|---|---|
| 0093269 | 4/1983 | European Pat. Off. . |
| 0091792A3 | 7/1983 | European Pat. Off. . |
| 2320253 | 1/1974 | France . |

Primary Examiner—David T. Fidei

[57] ABSTRACT

A package is provided for retaining a plurality of surgical sutures which includes a housing and a plurality of superimposed suture retainer reels disposed within the housing. Each of the suture retainer reels has a peripheral channel defined therein for maintaining a wound suture in such a manner so that the wound suture in one of said peripheral channels is disposed in an annular vertical plane which is substantially distinct from the annular vertical plane in which an adjacent wound suture is disposed. Structure is associated with the housing for maintaining the suture retainer reels in superimposed relationship. The package may also be provided with a needle park for releasably maintaining surgical needles in a position for ready removal.

19 Claims, 5 Drawing Sheets

FIG.1
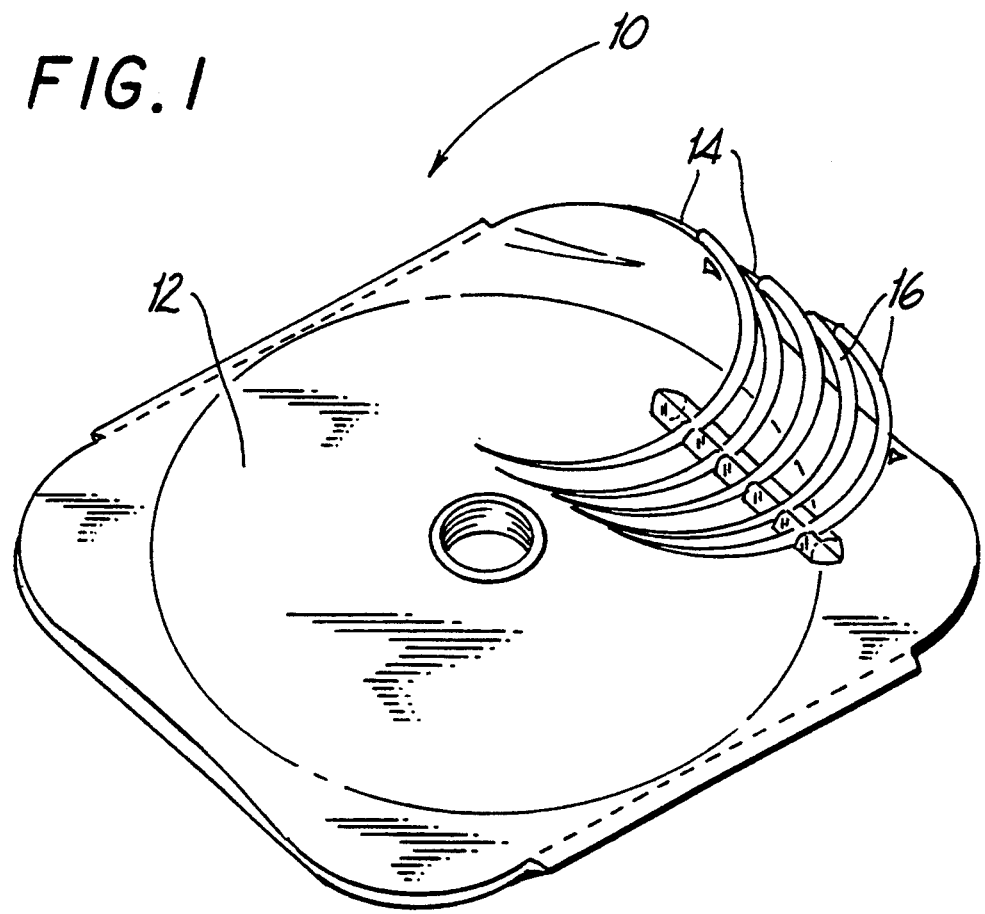
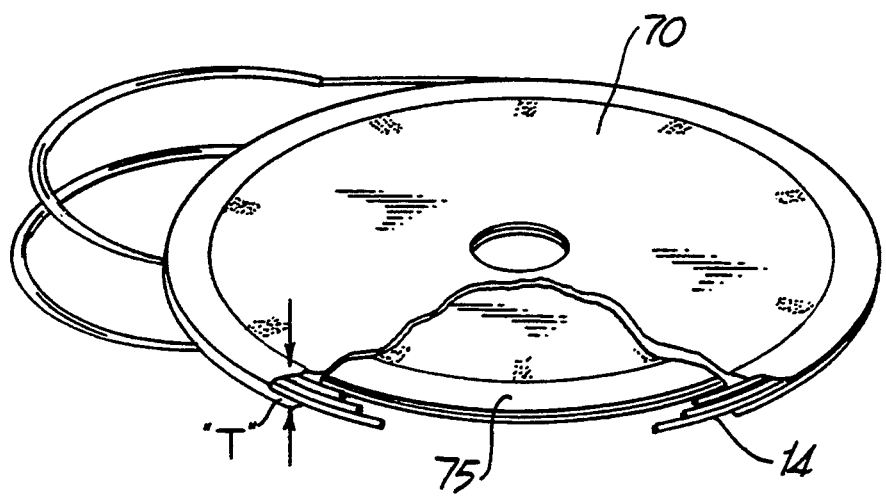
FIG.5

PACKAGE FOR RETAINING SURGICAL SUTURES

BACKGROUND OF THE INVENTION

1. Field of the Invention

The subject invention relates to packages for surgical sutures and more particularly to a package for retaining a plurality of surgical sutures in a manner for ready removal.

2. Description of Related Art

Retainer packages for surgical sutures are well known in the art. In the past, surgical sutures have been wound on reels disposed within packaging enclosures for ready removal. For example, U.S. Pat. No. 3,545,608 which issued to Berger, describes a retainer package having a plurality of identical cylindrical suture reels stacked within a recess formed in a packaging enclosure. Each of the cylindrical suture reels has an annular groove formed therein for receiving a surgical suture. However, the depth of the annular groove on each of the cylindrical suture reels is identical. Consequently, upon stacking the cylindrical suture reels within their housing, the combined thickness results in a relatively large package being required for accommodating a plurality of suture reels. Additionally, by forming the cylindrical suture reels in this manner, the area which lies radially inward of the annular groove remains unoccupied once loaded, and thus results in an inefficient use of space. Furthermore, since the annular groove in each of the suture reels is aligned and parallel to the annular grooves in adjacent retainer reels, there may be a tendency for sutures to become entangled with one another as they are unwound from their respective suture reels.

Accordingly, it is an object of the subject invention to provide a retainer package for housing a plurality of concentrically stacked suture retainer reels being formed in such a manner so as to make more efficient use of the thickness of the retainer package in which they are housed.

It is another object of the subject invention to provide a retainer package for housing a plurality of concentrically stacked suture retainer reels, which reels decrease the likelihood of sutures becoming tangled with one another upon being removed from the package.

It is yet another object of the subject invention to provide a lightweight and inexpensive suture retainer package for efficiently housing a plurality of surgical sutures.

These and other objects of the subject invention will be made more apparent from the following description thereof.

SUMMARY OF THE INVENTION

The subject invention is directed to a package for retaining a plurality of surgical sutures for ready removal. The package comprises housing means having a substantially planer upper panel hingedly connected to a substantially planer lower panel. A plurality of superimposed suture retainer reels of substantially similar diameter are disposed concentrically within the housing means. Each of the superimposed suture retainer reels has a peripheral channel defined therein for receiving a surgical suture. The depth of the peripheral channel defined in each of the superimposed suture retainer reels is distinct from the depth of the peripheral channel defined in an adjacent suture retainer reel. Alternatively, the diameter of each of the superimposed suture retainer reels may be distinct from the diameter of an adjacent suture retainer reel. In this instance, the depth of the peripheral channel in each of the suture retainer reels can remain substantially the same. Both of these arrangements greatly increase the effective use of space within the package while decreasing the total thickness of the assembled package, reducing material costs, and preventing sutures from becoming entangled upon removal from the package. Moreover, this highly efficient package arrangement in which adjacent wound sutures are disposed in substantially distinct annular vertical planes ensures ease of use during a surgical operation as well as reductions in inventory space. Preferably, each of the suture retainer reels includes a top disc portion and a bottom disc portion mounted adjacent one another in such a manner so as to form a peripheral channel for receiving a surgical suture.

Additionally, means are associated with the housing means for maintaining the plurality of superimposed suture retainer reels in a superimposed relationship. Preferably, a cylindrical hub member is provided for concentrically maintaining the suture retainer reels while enabling independent rotation of each of the suture retainer reels relative to one another.

Further features of the invention will become more apparent from the following detaned description of the invention and the accompanying drawings.

BRIEF DESCRIPTION OF THE DRAWINGS

Preferred embodiments of the subject invention will be described hereinbelow with reference to the drawings wherein:

FIG. 1 is a perspective view of the suture retainer package in accordance with a preferred embodiment of the subject invention;

FIG. 5 is an enlarged perspective view partially cutaway of a pair of stacked suture retainer reels which are housed within the suture retainer package of FIG. 1;

DETAILED DESCRIPTION OF PREFERRED EMBODIMENTS

Figure 2:
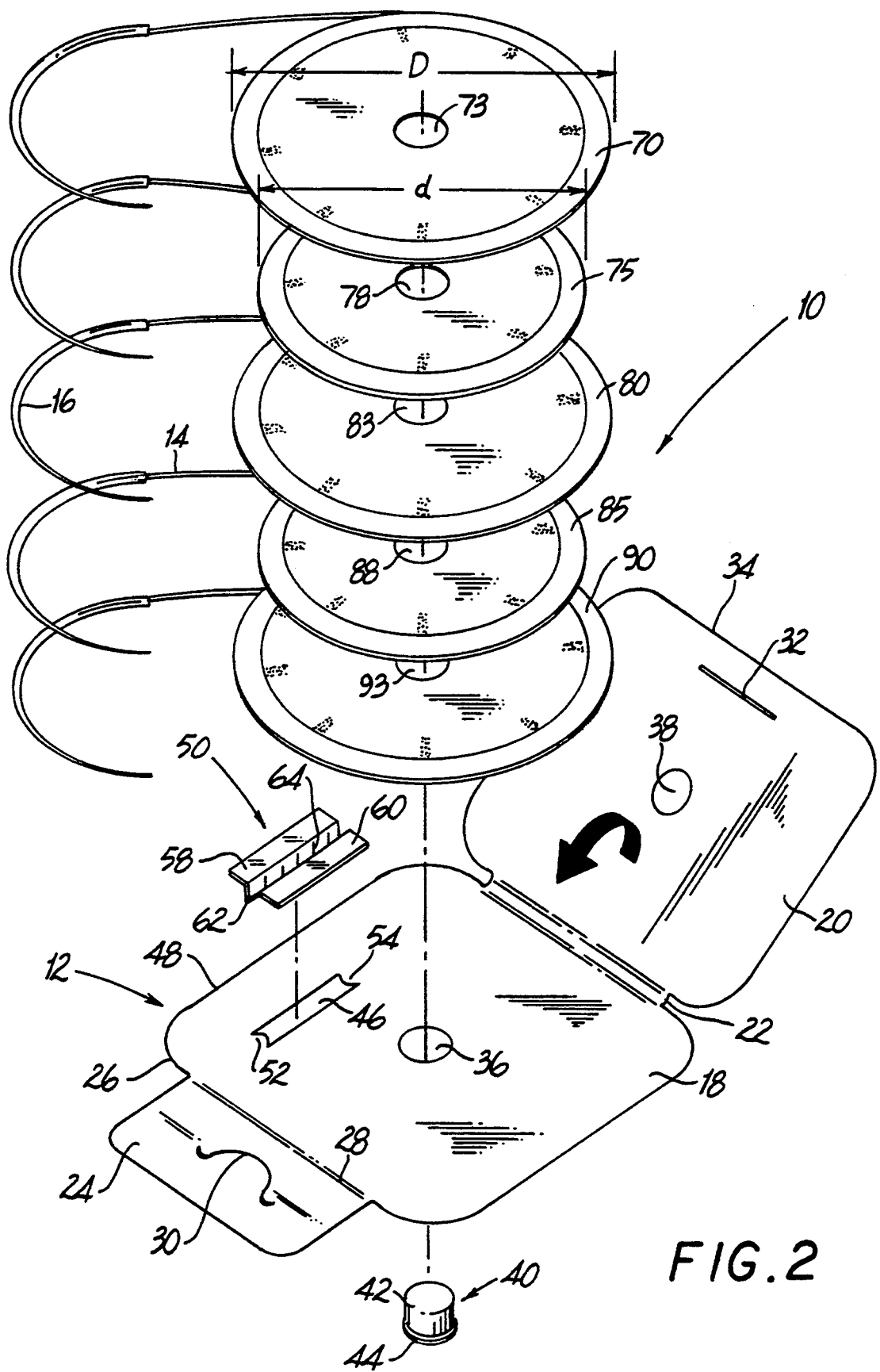
FIG. 2 is an exploded perspective view of the suture retainer package of FIG. 1.

A suture retainer package in accordance with a preferred embodiment of the subject invention is illustrated in FIG. 1 and is designated generally by reference numeral 10. Retainer package 10 comprises a housing 12, preferably constructed of a spun bonded polyolefin material such as Tyvek ® (available from DuPont). The housing 12 is particularly adapted to maintain, for ready removal, a plurality of surgical sutures 14 each having a surgical needle 16 affixed to an end thereof.

Referring to FIG. 2, the housing 12 has a substantially planar bottom panel 18 and a substantially rectangular planar top panel 20 which are hingedly connected to one another by hinge 22. A flap portion 24 is foldably connected along an outer edge 26 of bottom panel 18 and is foldable along a score line 28. A locking tab 30 is formed in the flap portion 24 of bottom panel 18 and is configured for engagement in a corresponding locking slit 32 provided in the top panel 20 adjacent an outer edge 34 thereof.

A circular aperture 36 is disposed in the bottom panel 18, and a corresponding circular aperture 38 is provided in the top panel 20. Circular apertures 36 and 38 are adapted to receive and maintain a hub member 40. Hub member 40 is preferably formed from a plastic material such as polyurethane, and has a cylindrical shaft portion 42 which extends through circular apertures 36 and 38. An annular flange portion 44 is configured to assist in mounting the hub member 40 within the apertures 36 and 38.

The bottom panel 18 of the housing 12 includes an elongated mounting slot 46 adjacent the lateral edge 48 of bottom panel 18 for receiving a needle park member 50. Mounting slot 46 is optionally provided with opposed tangs 52 and 54 which assist in retaining the needle park member 50 within mounting slot 46. Other mounting means are also envisioned by the present invention including sonic welding, adhesives, etc.

The needle park 50 is preferably formed from a substantially rectangular planar piece of plastic material having a plurality of score lines provided thereon about which the planar material is folded to define a structure having a pair of opposed mounting wings 58 and 60 separated by a substantially V-shaped channel portion 62. A plurality of apertures 64 are provided in the V-shaped channel portion 62 of needle park member 50 transverse to channel portion 62 for receiving and releasably retaining a plurality of surgical needles 16. Upon mounting the needle park member 50 in the mounting slot 46, the V-shaped channel portion 62 thereof is engaged by the opposed tangs 52 and 54 to be securely maintained within the retainer package 10.

The retainer package 10 of the subject invention further comprises a plurality of superimposed, substantially circular, suture retainer reels 70, 75, 80, 85, and 90, each of which is designed to retain a respective surgical suture 14. Suture retainer reels 70, 75, 80, 85, and 90 each comprise two planar disc portions which, like the housing 12, are also preferably constructed of Tyvek ®.

Figure 3:
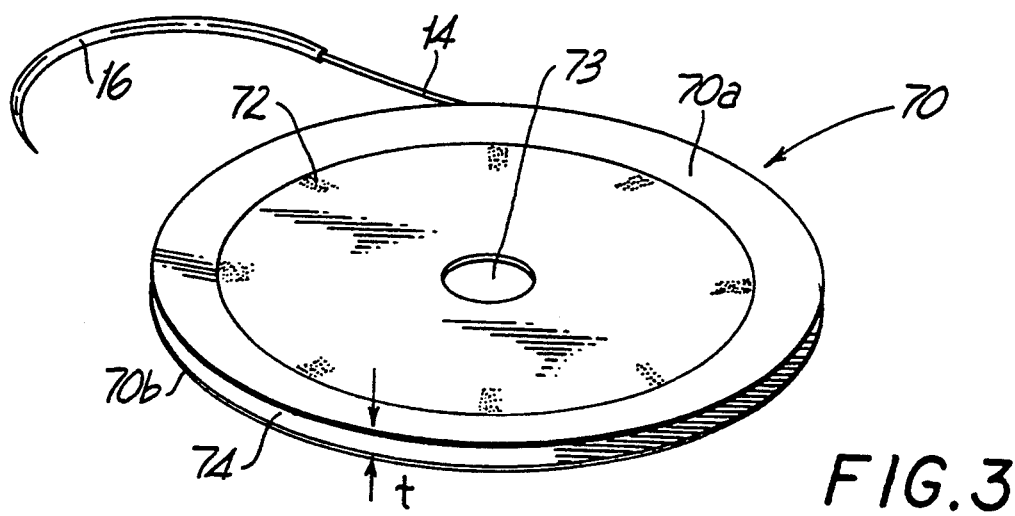
FIG. 3 is an enlarged perspective view of one of the suture retainer reels housed within the suture retainer package of FIG. 1.
Figure 4:
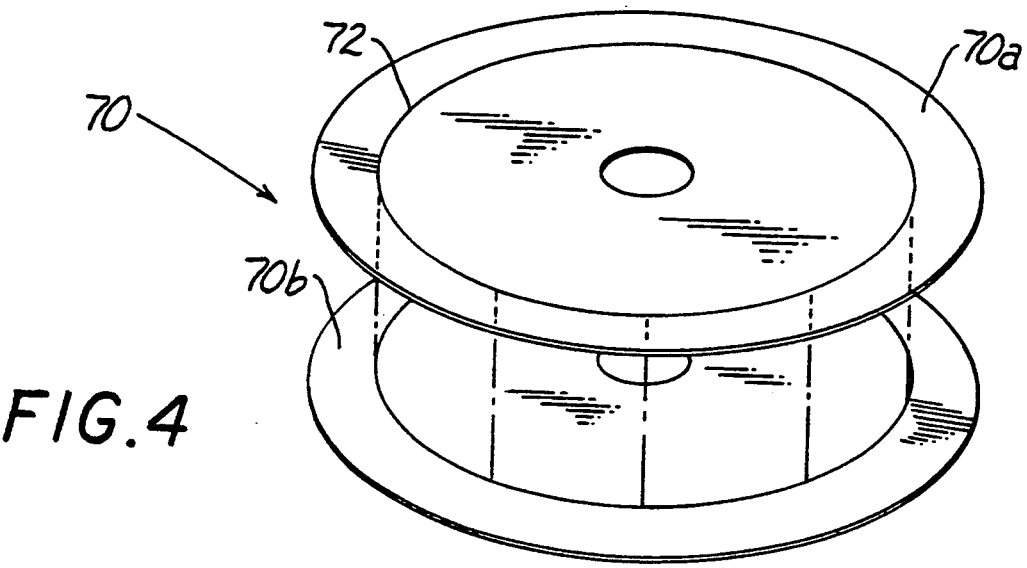
FIG. 4 is an exploded perspective view of the suture retainer reel of FIG. 3.

Referring to FIGS. 3 and 4, for example, channel member 70 has an upper disc portion 70a, and a lower disc portion 70b which are mounted adjacent one another about an annular weld-line 72. The annular weld-line 72 is spaced radially inward from the periphery of the suture retainer reel 70 to define a peripheral retaining channel 74. This construction is particularly adapted for winding a suture 14 in a substantially flat, increasing spiral pattern. The resulting spiral of gradually increasing diameter, which is preferably not greater than one suture diameter in height, ensures that a suture 14 is firmly held between the upper and lower disc portions 70a and 70b of retainer reel 70. As a result, a very flat suture retainer reel is provided even after a suture 14 is wound thereon.

Turning again to FIG. 2, adjacent suture retainer reels may have diameters which are distinct from one another and peripheral channels of substantially equal radial depth for decreasing the overall thickness of the retainer package 10. More specifically, suture retainer reels 70, 80 and 90 each have a diameter "D" which is greater than the diameter "d" of suture retainer reels 75 and 85. Therefore, as best seen in FIG. 5, upon assembly, two adjacent loaded suture retainer reels (e.g., suture retainer reels 70 and 75) would have an axial thickness "T" which is substantially equal to the axial thickness "t" of a single loaded suture retainer reel (FIG. 3), since a loaded suture retainer reel having a diameter "d" (suture retainer reels 75 and 85) would fit well within the circumference of the peripheral channel of a suture retainer reel having a diameter "D" (suture retainer reels 70, 80 and 90). Furthermore, suture retainer reels 70, 75, 80, 85 and 90 are each provided with an axial circular aperture 73, 78, 83, 88 and 93, respectively, for mounting on the cylindrical shaft portion 42 of hub member 40 in a superimposed manner.

To assemble the suture retainer package 10 of the subject invention, an armed surgical suture is wound on to each of the suture retainer reels 70, 75, 80, 85 and 90. The retainer reels 70, 75, 80, 85, and 90 are then mounted on hub member 40 so that the total axial thickness of the five mounted retainer reels is approximately equal to three times the axial diameter of a single suture 14, or stated differently three times the axial thickness "t" of a single loaded suture retainer reel (FIG. 3). Once mounted on hub member 40, the retainer reels may be packed tightly together for minimizing the total height of the package 10. Where the retainer reels are packaged tightly together it is not necessary that they be independently rotatable with respect to adjacent reels since the wound suture would simply slidably unwind from the reel when subject to a pulling force. Alternatively, where independent rotation of the reels is desired, the retainer reels may be packed loosely so as to enable independent rotation of each of the retainer reels relative to one another. In either instance, the arrangement of the superimposed suture retainer reels represents an efficient space saving packaging scheme. Moreover, by staggering adjacent retainer reels so that adjacent wound sutures are disposed in distinct annular vertical planes, the likelihood of sutures becoming entangled upon removal from the package is minimized.

This efficient, space saving package further translates into substantial savings in bulk inventory space both at the manufacturing facility and in transportation as well as in the hospitals. For example, where five sutures are packaged in the same space as three conventionally packaged sutures, a space saving of at least about 40% is achieved. Thus, 40% less storage space is necessary to maintain the same number of packaged sutures.

Figure 6:
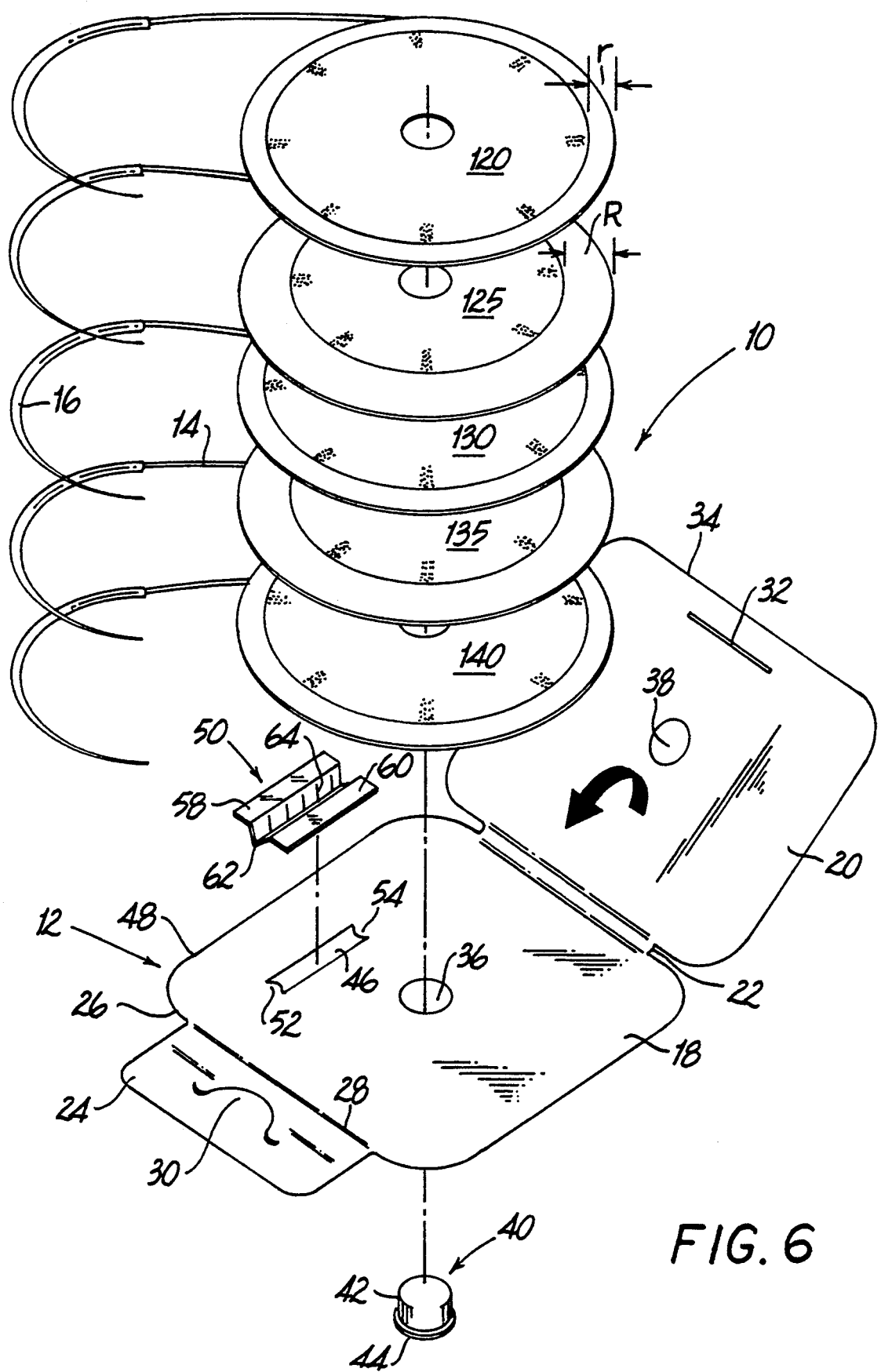
FIG. 6 is an exploded perspective view of an alternate embodiment of the suture retainer package in accordance with the subject invention.

Referring to FIG. 6 another embodiment of the suture retainer package of the subject invention may include a plurality of superimposed suture retainer reels 120, 125, 130, 135 and 140, each of which is designed to retain a respective surgical suture 14. Unlike the previous embodiment, the suture retainer reels of this embodiment are of substantially equal diameter. However, the radial depth of the peripheral channel of each of the suture retainer reels is distinct from the radial depth of the peripheral channel formed in an adjacent suture retainer reel. More specifically, suture retainer reels 120, 130 and 140 are each formed with a peripheral channel having a radial depth "r", which is less than the radial depth "R" of the peripheral channel defined in suture retainer reels 125 and 135. Therefore, upon assembly, two adjacent loaded suture reels (e.g., suture reels 120 and 125) would have an axial thickness which is substantially equal to the axial thickness of a single loaded suture retainer reel, since a suture wound in a peripheral channel with a radial depth "R" (suture retainer reels 125 and 135) would fit well within the radially inner circumference of the peripheral channel having a radial depth "r" (suture retainer reels 120, 130 and 140).

After the suture retainer reels have been mounted, the top panel 20 of the suture retainer package 10 may be folded over the superimposed retainer reels, followed by the flap portion 24 being folded over the top panel 20. At such a time, the locking tab 30 on the flap portion 24 can be engaged within the locking slit 32 on top panel 20 to maintain the retainer package 10 in a closed condition. Where armed sutures are to be retained, the needles are placed adjacent one another in apertures 64 of needle park 50. Preferably, apertures 64 are formed transverse to channel 62 and extend to an outside edge thereof to permit the needles to be easily pushed into the apertures without undue manipulation.

Figure 7:
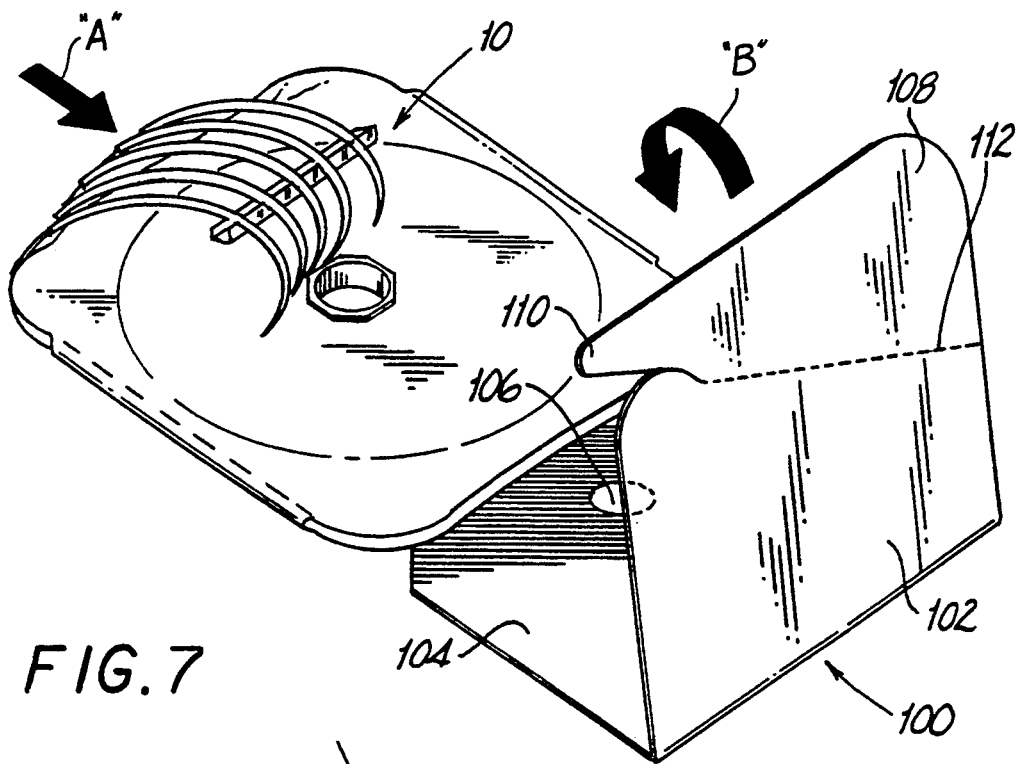
FIG. 7 is a perspective view of the suture retainer package of FIG. 1, and an accompanying packaging card.
Figure 8:
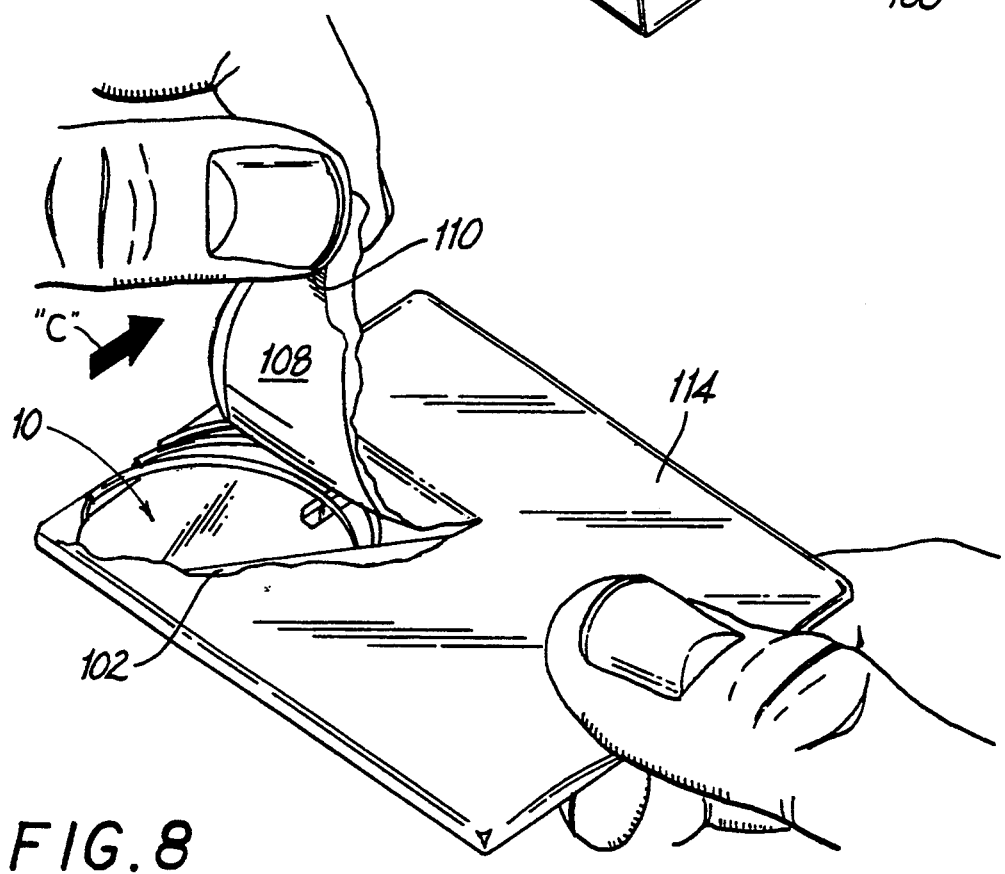
FIG. 8 is a perspective view illustrating the opening of a sterile pouch containing the suture retainer package and packaging card of FIG. 7.

Referring to FIGS. 7 and 8, subsequent to the retainer package 10 being assembled, it may be inserted into a folded loading card 100 as indicated by arrow "A". Loading card 100 has a top face 102 foldable upon a bottom face 104 as shown by indicator arrow "B". The bottom face 104 has a circular aperture 106 defined therein for accommodating the hub member 40 of suture retainer package 10. A pull tab portion 108 having an outwardly protruding section 110 is formed on the top face 102 along a perforation line 112. Pull tab 108 functions as a mechanism for opening a sterile foil pouch 114 within which the retainer package 10 is stored. More particularly, a user may grasp a section 110 of pull tab 108, and subsequently draw the pull tab 108 laterally along the perforation line 112 in the direction of indicator arrow "C", concurrently ripping the foil pouch 114 in such a manner so as to access the suture retainer package 10 therein.

While the invention has been described with respect to the preferred embodiment, it is apparent that changes may be made thereto without departing from the spirit or scope of the invention as defined by the appended claims.

What is claimed is:

1. A package for retaining a plurality of surgical sutures comprising:
   a housing;
   a plurality of superimposed suture retainer reels disposed in said housing including first through fifth suture retainer reels of substantially equal diameter in stacked, aligned relation from first to fifth, each of said reels having a peripheral channel defined therein configured to accommodate a surgical suture, the peripheral channel in said first, third and fifth retainer reels having a radial depth that is greater than the radial depth of the peripheral channel defined in said second and fourth suture retainer reels; and
   a supporting hub associated with said housing for maintaining said plurality of suture retainer reels in superimposed coaxial relationship.

2. A package as recited in claim 1, wherein said housing includes a substantially planar top portion and a substantially planar bottom portion, said top portion and said bottom portion being hingedly connected to one another.

3. A package as recited in claim 2, wherein said housing is of unitary construction.

4. A package as recited in claim 1, wherein said supporting hub comprises a substantially cylindrical hub member retainable in said housing.

5. A package as recited in claim 4, wherein said hub member is configured for permitting independent rotation of each of said plurality of suture retainer reels relative to one another.

6. A package as recited in claim 1, wherein each of said plurality of suture retainer reels includes a top disc portion and a bottom disc portion mounted adjacent one another to define said peripheral channel.

7. A package as recited in claim 1, wherein each of said plurality of suture retainer reels are substantially circular in configuration.

8. A package as recited in claim 1, further comprising a needle park including means for maintaining a plurality of surgical needles in a position for ready removal.

9. A package as recited in claim 8, wherein said needle park releasably maintains said plurality of surgical needles in substantially spaced relation.

10. A package for retaining a plurality of surgical sutures comprising:
    a housing;
    a plurality of superimposed suture retainer reels disposed in said housing including first through fifth suture retainer reels in stacked, aligned relation from first to fifth, each of said suture retainer reels having a peripheral channel of substantially equal depth defined therein configured to accommodate a surgical suture, said first, third, and fifth retainer reels each having a diameter that is greater than the diameter of said second and fourth suture retainer reels; and
    a supporting hub associated with said housing for maintaining said plurality of suture retainer reels in superimposed coaxial relationship.

11. A package as recited in claim 10, wherein said suture retainer reels each have a peripheral channel of substantially equal radial depth defined therein.

12. A package as recited in claim 10, wherein said housing includes a substantially planar top portion and a substantially planar bottom portion, said top portion and said bottom portion being hingedly connected to one another.

13. A package as recited in claim 10, wherein said housing is of unitary construction.

14. A package as recited in claim 10, wherein said supporting hub comprises a substantially cylindrical hub member retainable in said housing.

15. A package as recited in claim 14, wherein said hub member is configured for permitting independent rotation of each of said plurality of suture retainer reels relative to one another.

16. A package as recited in claim 10, wherein each of said plurality of suture retainer reels includes a top disc portion and a bottom disc portion mounted adjacent one another to define said peripheral channel.

17. A package as recited in claim 10, wherein each of said plurality of suture retainer reels are substantially circular in configuration.

18. A package as recited in claim 10, further comprising a needle park including means for maintaining a plurality of surgical needles in a position for ready removal.

19. A package as recited in claim 18, wherein said needle park releasably maintains said plurality of surgical needles in substantially spaced relation.

* * * * *